United States Patent

Fuchs et al.

[11] 4,039,668
[45] Aug. 2, 1977

[54] CORTICOID-CONTAINING INHALANTS

[75] Inventors: Peter Fuchs; Erich Gerhards; Heinz Matthes; Hans Wendt; Rudolf Wiechert, all of Berlin, Germany

[73] Assignee: Schering Aktiengesellschaft, Berlin & Bergkamen, Germany

[21] Appl. No.: 714,668

[22] Filed: Aug. 16, 1976

Related U.S. Application Data

[63] Continuation of Ser. No. 481,830, June 21, 1974, abandoned.

[30] Foreign Application Priority Data

June 23, 1973 Germany .............................. 2332663

[51] Int. Cl.$^2$ .............................................. A61K 31/58
[52] U.S. Cl. .................................................. 424/241
[58] Field of Search ......................................... 424/241

[56] References Cited

U.S. PATENT DOCUMENTS

| | | | |
|---|---|---|---|
| 3,073,743 | 1/1963 | Spero................................ | 260/397.45 |
| 3,824,260 | 7/1974 | Laurent............................. | 260/397.45 |
| 3,906,095 | 9/1975 | Laurent et al. ................... | 260/397.1 |
| 3,944,577 | 3/1976 | Laurent et al. ..................... | 424/243 |

Primary Examiner—Elbert L. Roberts
Attorney, Agent, or Firm—Millen & White

[57] ABSTRACT

Inhalants comprising at least one corticoid of the general formula

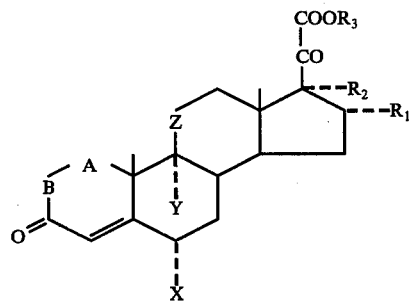

wherein —B—A— is $CH_2$—$CH_2$—, $CH=CH$— or $CCl=CH$—; X is a hydrogen atom, a fluorine atom, or methyl; Y is a hydrogen atom, a fluorine atom or a chlorine atom; Z is methylene, hydroxymethylene, fluoromethylene, a chloromethylene, or carbyl; $R_1$ is a hydrogen atom or methyl and $R_2$ is a hydrogen atom, or $R_1$ and $R_2$ collectivey are isopropylidenedioxy; and $R_3$ is hydrocarbon of 1–12 carbon atoms, are useful for the treatment of allergic diseases of the respiratory tract.

10 Claims, No Drawings

CORTICOID-CONTAINING INHALANTS

This is a continuation, of application Ser. No. 481,830 filed June 21, 1974 now abandoned.

BACKGROUND OF THE INVENTION

This invention relates to a process for the treatment of allergic diseases of the respiratory passage and to cortencoid-containing inhalants useful therein.

It is known that corticoid-containing medicinal agents can be employed for the treatment of allergic diseases of the respiratory passage, such as, for example, rhinitis or bronchial asthma. However, the use of these drugs for the treatment of such diseases is not free from objection, in spite of their effectiveness, because corticoids used for this purpose often cause, in higher dosages and with long-term treatment, grave side effects in many cases, such as, for example, the so-called Cushing's syndrome (Brit. Med, J., 1966, 2, 796; and The Lancet, 1970, 733).

Compounds of Formula I hereinafter wherein $R_2$ is a hydrogen atom are disclosed in Application Ser. No. 284,710, filed Aug. 30, 1972, now U.S. Pat. No. 3,824,260, and Application Ser. No. 460,905, filed Apr. 15, 1974, now U.S. Pat. No. 3,956,347 whose disclosures are incorporated by reference, as having topical anti-inflammatory activity but lacking systemic activity. Application Ser. No. 459,412 filed Apr. 9, 1974, now U.S. Pat. No. 3,906,095 is directed to pharmaceutical compositions comprising them adapted for topical administration and to the use thereof for the topical treatment of inflammation. Compounds of Formula I wherein $R_1$ and $R_2$ collectively are isopropylenedioxy are disclosed in Application Ser. No. 426,702, filed Dec. 20, 1973, now U.S. Pat. No. 3,919,421 having good topical anti-inflammatory activity but lacking systemic activity. There is no disclosure in these application concerning the effectiveness of these corticoid steroids in the treatment of allergic diseases of the respiratory allergic diseases, the applications being directed to the treatment of diseases of the skin.

In order to mitigate the side effects occurring in the treatment of allergic diseases of the respiratory passages with corticoids, the practice was adapted to administer the corticoids in the form of aerosol inhalants, rather than orally as heretofore. See The Lancet, 163,147; Arch. Intern. Med., 115 [1965] 602; Brit. Med. C., 1972, 1, 585. Although it was possible to reduce the incidence of side effects with this form of application, it was impossible to eliminate the undesired side effects, because during inhaling a portion of the inhalant always enters the gastrointestinal tract and is absorbed systemically.

It is an object of the present invention to provide a method for the corticoid treatment of allergic diseases of the respiratory passages which is substantially free of undesired corticoid side-effects and to corticoid-containing inhalants useful therein.

SUMMARY OF THE INVENTION

In its composition aspects, this invention relates to corticoid-containing inhalants comprising at least one corticoid of the general formula

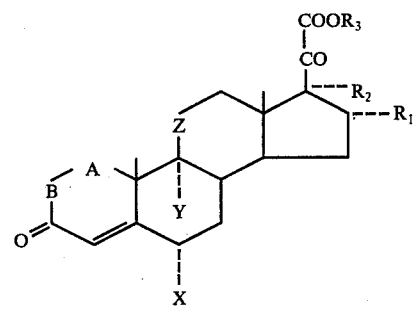

wherein —B—A— is —$CH_2$—$CH_2$—, —CH=CH— or —CCl=CH—; X is a hydrogen atom, a fluorine atom, or methyl; Y is a hydrogen atom, a fluorine atom or a chlorine atom; Z in methylene, hydroxymethylene, fluromethylene, a chloromethylene, or carbonyl; $R_1$ is a hydrogen atom or methyl and $R_2$ is a hydrogen atom, or $R_1$ and $R_2$ collectively are isopropylidenedioxy; and $R_3$ is hydrocarbon of 1–12 carbon atoms.

In its method-of-use aspect, this invention relates to a method of treating allergic diseases of the respiratory tract which comprises administering to the patient by inhalation an effective amount of a compound of Formula I.

DETAILED DISCUSSION

Of the compounds of Formula I, pereferred are those wherein:
  a. $R_1$ is $CH_3$ and $R_2$ is H;
  b. —B—A— is —CH=CH—, especially those of (a);
  c. X is F, especially those of (a) and (b);
  d. Z is β-hydroxymethylene, esceecially those of (a), (b) and (c);
  e. Z is F or Cl and Y is Cl, especially those of (a), (b) and (c);
  f. Z is $CH_2$ and Y is H, especially those of (a), (b) and (c);
  g. $R_3$ is lower-alkyl, preferably butyl or isobutyl, especially those of (a), (b), (c), (d), (e) and (f).

$R_3$ can be any aliphatic, aromatic, cycloaliphatic, saturated or unsaturated group of 1–12 carbon atoms, preferably 1–6 carbon atoms. Examples of $R_3$ are alkyl, alkenyl, cycloalkyl and cycloalkenyl, methyl, ethyl, propyl, allyl, cyclopropyl, isopropyl, propinyl, butyl, sec.-butyl, tert.-butyl, butyl-(2), cyclobutyl, pentyl, isopentyl, tert.-pentyl, 2-methybutyl, cyclopentyl, hexyl, cyclohexyl, cyclohex-2-enyl, cyclopentyl-methyl,heptyl, octyl, bornyl, isobornyl, menthyl, nonyl, decyl, dodecyl and aralkyl, e.g., benzyl, 2-phenylethyl, 3-phenylpropyl, 3-phenylprop-2-enyl.

Examples of possible effective agents for the corticoid-containing inhalants of this invention are set forth below:

The following esters of 6α-fluoro-11β-hydroxy-3,20-dioxo-16α-methyl-1,4-pregandiene-21-oic acid:
  methyl ester,
  ethyl ester,
  propyl ester,
  isopropyl ester,
  butyl ester,
  pentyl ester,
  hexyl ester,
  decyl ester,
  tert.-butyl ester,
  cyclobutyl ester,
  cyclohexyl ester, benzyl ester,
2'-propenyl ester,
2'-propinyl ester,
3'-butenyl ester,
3'-butinyl ester, and
menthyl ester;
the methyl ester of 6α-fluoro-2-chloro-11β-hydroxy-3,20-dioxo-16α-methyl-1,4-pregnadiene-21-oic acid;
the methyl ester of 6α-fluoro-9α-chloro-11β-hydroxy-3,20-dioxo-16α-methyl-1,4-pregnadiene-21-oic acid;
the butyl ester of 6α-fluoro-9α-chloro-11β-hydroxy-3,20-dioxo-16α-methyl-1,4-pregnadine-21-oic acid;
the isobutyl ester of 6α-fluoro-9α-chloro-11β-hydroxy-3,20-dioxo-16α-methyl-1,4-pregnadiene-21-oic acid;
the methyl ester of 6α,9α-difluro-11α-hydroxy-3,20-dioxo-16α-methyl-1,4-pregnadiene-21-oic acid;
the ethyl ester of 6α,9α-difluro-11β-hydroxy-3,20-dioxo-16α-methyl-1,4-pregnadiene-21-oic acid;
the butyl ester of 6α,9α-difluoro-11β-hydroxy-3,20-dioxo-16α-methyl-1,4-pregnadiene-21-oic acid;
the methyl ester of 6α,11β-difluoro-9α-chloro-3,20-dioxo-16α-methyl-1,4-pregnadiene-21-oic acid;
the butyl ester of 6α,11β-difluoro-9α-chloro-3,20-dioxo-16α-methyl-1,4-pregnadiene-21-oic acid;
the methyl ester of 6α-fluoro-9α,11β-dichloro-3,20-dioxo-16α-methyl-1,4-pregnadiene-21-oic acid;
the butyl ester of 6α-fluoro-9α,11β-dichloro-3,20-dioxo-16α-methyl-1,4-pregnadiene-21-oic acid;
the methyl ester of 9α-fluoro-11β-hydroxy-3,20-dioxo-16α-methyl-1,4-pregnadiene-21-oic acid;
the butyl ester of 9α-fluoro-11β-hydroxy-3,20-dioxo-16α-methyl-1,4-pregnadiene-21-oic acid;
the butyl ester of 11β-hydroxy-3,20-dioxo-16α-methyl-1,4-pregnadiene-21-oic acid;
the methyl ester of 11β-hydroxy-3,20-dioxo-1,4-pregnadiene-21-oic acid;
the butyl ester of 11β-hydroxy-3,20-dioxo-1,4-pregnadiene-21-oic acid;
the butyl ester of 6α-fluoro-11β-hydroxy-3,20-dioxo-16α-methyl-4-pregnene-21-oic acid;
the butyl ester of 6α-fluoro-3,20-dioxo-16α-methyl-4-pregnene-21oic acid;
the butyl ester of 3,20-dioxo-16α-methyl4pregnene-21oic acid;
the methyl ester of 6α-fluoro-3,11,20-trioxo-16α-methyl-1,4-pregnadiene-21-oic acid;
the butyl ester of 6α-fluoro-3,11,20-trioxo-16α-methyl-1,4-pregnadiene-21-oic acid;
the methyl ester of 11β-hydroxy-3,11,20-dioxo-4-pregnene-21-oic acid;
the butyl ester of 6α-fluoro-3,11,20-trioxo-16α-methyl-4-pregnene-21-oic acid;
the methyl ester of 9α-fluoro-11β-hydroxy-3,20-dioxo-16α,17α-isopropylidenedioxy-1,4-pregnadiene-21-oic acid;
the ethyl ester of 9α-fluoro-11β-hydroxy-3,20-dioxo-16α,17α-isopropylidenedioxy-1,4-pregnadiene-21-oic acid;
the butyl ester of 9α-fluoro-11β-hydroxy-3,20-dioxo-16α,17α-isopropylidenedioxy-1,4-pregnadiene-21oic acid; and
the butyl ester of 11β-hydroxy-3,20-dioxo-6α,16α-dimethyl-1,4-pregnadiene-21-oic acid.

The active corticoid agents used for the inhalants of this invention are described, inter alia, in the following patent applications German P 21 50 268 and U.S. Ser. No. 284,710filed Aug. 30, 1972; German 22 04 361; German 22 64 003; and U.S. Ser. No. 426,702 filed Dec. 20, 1973; German Pat. 23 19 479; German 23 19 479; and U.S. Ser. No. 460,905 filed Apr. 15, 1974, and also Belgian Pat. No. 779,869. These compounds can be prepared, for example, by the method disclosed in Belgian Pat. No. 779,869 and the above-identified applictions.

To produce the inhalants of this invention, an active corticoid agent of Formula I is conventionally pulverized or dissolved or suspended in a suitable solvent, and optionally combined with one or more suitable additives, e.g., diluents, thickeners, auxiliary suspension agents, propellant gases, flavor-ameliorating agents. Usually, one corticoid or a mixture of two corticoids is utilized as the active agents for the inhalants, but it is also possible to formulate inhaling agents containing, in addition to an active corticoid agent, also other auxiliary effective agents, e.g., antibiotics, for example, chloramphenicol, tetracyclines, penicillins, cephalosporins, lincomycins, erythromycins, and rhifamycins.

Thus, for example, the active corticoid agents can be dissolved in a physiologically compatible solvent, such as e.g., water or alcohol or suspended therein and then combined optionally with the customary additives.

The thus-obtained solutions or suspensions, containing preferably 0.01–10% of the active corticoid agent, are administered by inhalation, usually with the aid of a conventional inhalator.

The active corticoid agent can also be suspended or dissolved, optionally with the customary additives, in a physiologically acceptable propellant gas, for example, "Frigen" ("Freon" ), and the thus-produced suspensions or solutions can be filled into spray cans, preferably provided with a dosing valve. The thus-obtained inhalants, containing preferably 0.01 –10% of the active corticoid agent, are administered in the usual manner.

For atomization in the dry form, it is especially advantageous to provide the active corticoid agents at an average particle size of 0.01 – 20 μ, e.g., by micronizing or precipitation.

In order to increase the shelf life and the facilitate the aerosol formation, these pulverized corticoids are advantageously combined with a solid, pharmacologically inert, watersoluble, pulverulent carrier having an average particle size of 20– 200 μ. Examples of suitable carriers are dextran, mannitol, glucose, or lactose. These powdery inhalants, to which can also be admixed further additives, such as, for example, flavor-ameliorating agents (e.g., saccharin), or antibiotics (e.g., a penicillin, a tetracycline, or an erythromycin), contain customarily from 0.1% of active corticoid agent. The production of pulverulent inhalants and their application are described, for example in German Unexamined Laid-Open Applications DOS 17 92 207 and 22 29 981.

The inhalants of the present invention can be utilized, as mentioned above, for the treatment of allergic diseases of the respiratory passages, such as, for example, rhinitis-type diseases, hay fever, or bronchial asthma, by the inhalation thereof by the effected patient.

The quantity of inhalant to be administered daily per inhalation varies on dependence of the graveness of the diseases and the constitution of the person being treated. Customarily, about 0.01 – 100 mg. and preferably 0.1 –10 mg. of active corticoid agent is administered per inhalation. The daily dosage is usually 0.02 – 1000 mg. and preferably 0.1 – 50 mg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius, unless otherwise indicated, all parts and percentages are by weight.

EXAMPLE 1

1,000 g. of micronized butyl ester of 6α-fluoro-11-β-hydroxy-3,20-dioxo-16α-methyl-1,4-pregnadiene-21-oic acid (average particle size: smaller than 7 μ) and 39,000 g. of ground lactose are mixed together. Respectively 40 mg. of the mixture is filled into mating capsules. The inhalant can be administered, after opening the capsule, by inhaling, preferably sniffing, or a "Spinhaler" is used to administer the inhalant.

EXAMPLE 2

1,000 g. of micronized butyl ester of 6α-fluoro-9α,11β-dichloro-3,20-dioxo-16α-methyl-1,4-pregnadiene-21-oic acid (average particle size: smaller than 7 μ) and 39,000 g. of ground lactose are mixed together. Respectively 40 mg. of the mixture is filled into mating capsules. The inhalant can be administered, after opening the capsule, by inhaling, preferably sniffing, or a "Spinhaler" is utilized to apply the inhalant.

EXAMPLE 3

1,000 g. of micronized isobutyl ester of 6α-fluoro-9α-chloro-11β-hydroxy-3,20-dioxo-16α-methyl-1,4-pregnadiene-21-oic acid (average particle size: smaller than 7 μ) and 39,000 g. of ground lactose are mixed together. Respectively 40 mg. of the mixture are filled into mating capsules. The inhalant can be administered, after opening the capsule, by inhaling, preferably sniffing, or a "Spinhaler" is used to administer the inhalant.

EXAMPLE 4

A spray can, equipped with a metering valve (one dose =200 mg., corresponding to 1 mg. of active agent), is filled with 25 mg. of the butyl ester of 6α-fluoro-11β-hydroxy-3,20-dioxo16α-methyl-1,4-pregnadiene-21-oic acid and 5.0 ml. of "Freon"12/14 (40:60). The inhalant is administered in the usual manner.

EXAMPLE 5

A spray can, provided with a metering valve (one dose =200 mg., corresponding to 1 mg. of active agent), is filled with 25 mg. of the butyl ester of 6α,9α-difluoro-11β-hydroxy-3,20-dioxo-16α-methyl-1,4-pregnadiene-21-oic acid and 5.0 ml. of "Freon" 12/14 (40:60). The inhalant is administered in the usual manner.

EXAMPLE 6

0,100 g. of micronized butyl ester of 6α-fluoro-11β-hydroxy-3,20-dioxo-16α-methyl-1,4-pregnadiene-21-oic acid (average particle size: smaller than 7 μ) and 39,900 g. of ground lactose are mixed together. Respectively 40 mg. of the mixture is filled into mating capsules. The inhalant can be administered, after opening the capsule, by inhaling, preferably sniffing, or a "Spinhaler" is used to administer the inhalant.

EXAMPLE 7

2,000 g. of micronized butyl ester of 6α-fluoro-11β-hydroxy-3,20-dioxo-16α-methyl-1,4-pregnadiene-21-oic acid (average particle size: smaller than 7 μ) and 38,000 g. of ground lactose are mixed together. Respectively 40 mg. of the mixture is filled into mating capsules. The inhalant can be administered after opening the capsule, by inhaling, preferably sniffing, or a "Spinhaler" is used to administer the inhalant.

EXAMPLE 8

The inhalant described in Example 1 will be used in the long term therapy of allergic rhinitis. For this purpose adult patients sniff three times daily the contents of one capsule after opening it.

EXAMPLE 9

The inhalant described in Example 6 will be used in the long term therapy of allergic rhinitis. For this purpose children sniff three times daily the contents of one capsule after opening it.

EXAMPLE 10

The inhalant described in Example 7 will be used in the long term therapy of asthma bronchiale. For this purpose the inhalant is administered three times daily to adult patients by using a "Spinhaler".

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A corticoid-containing inhalant comprising, in admixture with a pharmaceutically acceptable carrier adapted for inhalation, an effective amount of at least one controlled of the formula

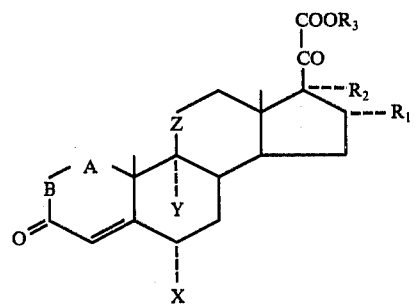

wherein —B—A— is —$CH_2$—$CH_2$—, —CH=CH— or —CCl=CH—; X is a hydrogen atom, a fluorine atom, or methyl; Y is a hydrogen atom, a fluorine atom or a chlorine atom; Z is methylene, hydroxymethylene, fluoromethylene, a chloromethylene, or carbonyl; $R_1$ is a hydrogen atom or methyl and $R_2$ is a hydrogen atom, or $R_1$ and $R_2$ collectively are isopropylidenedioxy; and $R_3$ is hydrocarbon of 1-12 carbon atoms.

2. An inhalant according to claim 1, wherein the corticoid has an average particle size of 0.01 - 20 μ.

3. An inhalant according to claim 1, comprising a solid, pharmcologically inert, water-soluble carrier having an average particle size of 20 - 200 μ.

4. An inhalant according to claim 3, wherein the solid, pharmacologically inert, water-soluble carrier is dextran, mannitol, or lactose.

5. An inhalant according to claim 1, wherein —B—A— is —CH=CH—, X is F, $R_1$ is $CH_3$ and $R_2$ is H.

6. An inhalant method according to claim 5, wherein $R_3$ is butyl or isobutyl.

7. A method for the treatment of an allergic disease of the respiratory passage, which comprises administering to the patient by inhalation an effective amount of at least one compounds of the formula

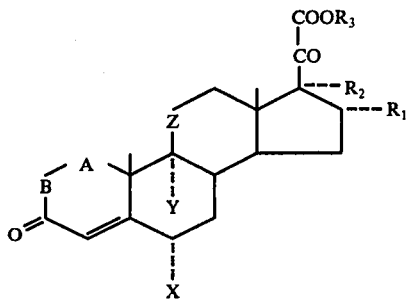

wherein —B—A— is —$CH_2$—$CH_2$—, —CH=CH— or CCl=CH—; X is a hydrogen atom, a fluorine atom, or methyl; Y is a hydrogen atom, a fluorine atom or a chlorine atom; Z is methylene, hydroxymethylene, fluoromethylene, a chloromethylene, or carbonyl; $R_1$ is a hydrogen atom or methyl and $R_3$ is a hydrogen atom, or $R_1$ and $R_2$ collectively are isopropylidenedioxy; and $R_3$ is hydrocarbon of 1-12 carbon atoms.

8. A method according to claim 7, wherein the corticoid is administered as solid particles having an average particle size of 0.01 - 20 μ.

9. A method according to claim 8, wherein the corticoid is administered in admixture with a solid, pharmacologically inert, water-soluble carrier having an average particle size of 20 - 200 μ.

10. A method according to claim 9 wherein —B—A— is —CH=CH—, X is F, $R_1$ is $CH_3$ and $R_2$ is H.

* * * * *

UNITED STATES PATENT AND TRADEMARK OFFICE
CERTIFICATE OF CORRECTION

PATENT NO. : 4,039,668
DATED : August 2, 1977
INVENTOR(S) : PETER FUCHS ET AL.

It is certified that error appears in the above–identified patent and that said Letters Patent are hereby corrected as shown below:

Claim 1, column 6, line 44: Please delete "controlled" and replace it with -- corticoid -- .

Signed and Sealed this

Twenty-second Day of November 1977

[SEAL]

Attest:

RUTH C. MASON
*Attesting Officer*

LUTRELLE F. PARKER
*Acting Commissioner of Patents and Trademarks*